(12) United States Patent
Cree et al.

(10) Patent No.: US 8,182,728 B2
(45) Date of Patent: May 22, 2012

(54) APERTURED MATERIAL FOR USE IN ABSORBENT ARTICLES

(75) Inventors: James W. Cree, Chesterfield, VA (US); Lino Iulianetti, Torre dei Passeri (IT)

(73) Assignee: Tredegar Film Products Corporation, Richmond, VA (US)

( * ) Notice: Subject to any disclaimer, the term of this patent is extended or adjusted under 35 U.S.C. 154(b) by 0 days.

(21) Appl. No.: 11/546,151

(22) Filed: Oct. 11, 2006

(65) Prior Publication Data

US 2007/0029694 A1  Feb. 8, 2007

Related U.S. Application Data

(62) Division of application No. 10/744,152, filed on Dec. 22, 2003, now abandoned.

(60) Provisional application No. 60/435,942, filed on Dec. 20, 2002.

(51) Int. Cl.
*B28B 1/48* (2006.01)

(52) U.S. Cl. .......... 264/156; 264/80; 264/154; 428/221; 428/131

(58) Field of Classification Search .................. 264/156, 264/80, 154, 138, 155, 284, 293, 294, 296, 264/280; 428/221, 131
See application file for complete search history.

(56) References Cited

U.S. PATENT DOCUMENTS

| | | | |
|---|---|---|---|
| 3,018,515 A * | 1/1962 | Sneddon | .......... 425/466 |
| 3,929,135 A * | 12/1975 | Thompson | .......... 604/385.08 |
| 3,945,386 A | 3/1976 | Anczurowski | |
| 3,967,623 A | 7/1976 | Butterworth | |
| 4,272,473 A | 6/1981 | Riemersma et al. | |
| 4,323,069 A | 4/1982 | Ahr | |
| 4,324,247 A | 4/1982 | Aziz | |
| 4,381,612 A * | 5/1983 | Shank | .......... 34/116 |
| 4,463,045 A | 7/1984 | Ahr et al. | |
| 4,629,643 A | 12/1986 | Curro et al. | |
| 4,637,819 A | 1/1987 | Ovellette et al. | |
| 4,644,623 A | 2/1987 | Raley et al. | |
| 4,726,976 A | 2/1988 | Karami | |
| 4,747,991 A | 5/1988 | Bishop | |
| 4,781,962 A | 11/1988 | Zamarripa et al. | |
| 4,839,216 A | 6/1989 | Curro et al. | |
| 5,043,115 A * | 8/1991 | Aoshima et al. | .......... 264/54 |
| 5,158,819 A | 10/1992 | Goodman, Jr. et al. | |
| 5,171,238 A | 12/1992 | Kajander | |
| 5,342,334 A | 8/1994 | Thompson | |
| 5,352,217 A | 10/1994 | Curro | |
| 5,368,909 A | 11/1994 | Langdon | |
| 5,439,458 A | 8/1995 | Noel | |
| 5,441,691 A | 8/1995 | Dobrin et al. | |
| 5,509,915 A | 4/1996 | Hanson | |
| 5,603,707 A | 2/1997 | Trombetta | |
| 5,614,283 A | 3/1997 | Potnis | |
| 5,643,240 A | 7/1997 | Jackson | |
| 5,846,230 A | 12/1998 | Osborn, III | |
| 6,228,462 B1 | 5/2001 | Lee et al. | |
| 6,348,253 B1 | 2/2002 | Daley et al. | |

(Continued)

FOREIGN PATENT DOCUMENTS

EP  0313 766  9/1988

(Continued)

*Primary Examiner* — Yogendra Gupta
*Assistant Examiner* — John Robitaille

(57) ABSTRACT

A method of thermo-mechanically forming macrotextures in a microtextured film wherein a heat shield is utilized to thermally insulate the microtexture during the forming process.

14 Claims, 3 Drawing Sheets

U.S. PATENT DOCUMENTS

| | | | |
|---|---|---|---|
| 6,599,612 B1 | 7/2003 | Gray | |
| 6,699,564 B2 * | 3/2004 | Hisanaka et al. | 428/138 |
| 2003/0121380 A1 * | 7/2003 | Cowell et al. | 83/30 |
| 2004/0119208 A1 * | 6/2004 | Gray et al. | 264/504 |
| 2004/0247857 A1 * | 12/2004 | Schroeder et al. | 428/319.1 |

FOREIGN PATENT DOCUMENTS

| | | |
|---|---|---|
| EP | 0399591 | 5/1990 |
| JP | 55111224 | 8/1980 |
| JP | 1101138 | 4/1989 |
| JP | 4-368846 | 12/1992 |
| JP | 2000177006 | 6/2000 |
| JP | 2001-504766 | 4/2001 |
| WO | WO 93/01047 | 1/1993 |
| WO | WO 99/00082 | 1/1999 |
| WO | WO 99/14039 | 3/1999 |
| WO | WO 99/30658 | 6/1999 |
| WO | WO 99/33640 | 7/1999 |
| WO | WO 01/56526 | 8/2001 |
| WO | WO 01/76842 | 10/2001 |
| WO | WO 02/098338 | 12/2002 |
| WO | WO 03/047489 | 6/2003 |

* cited by examiner

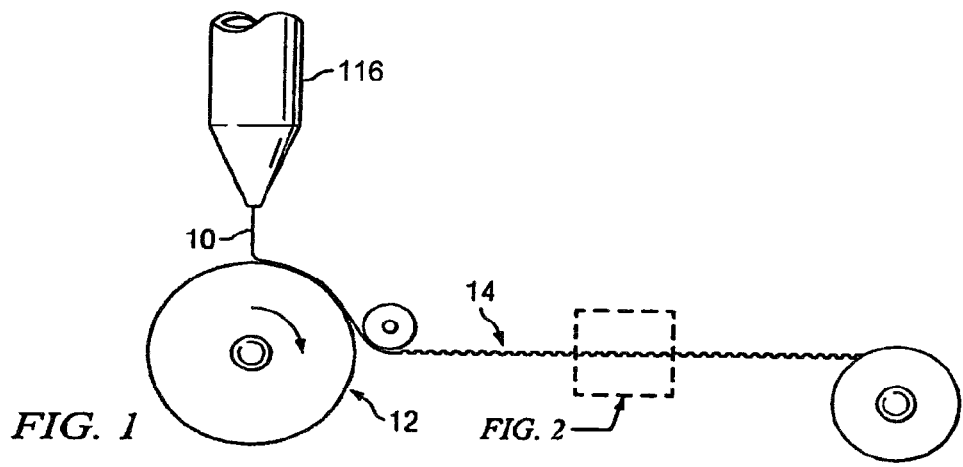
FIG. 1
FIG. 2
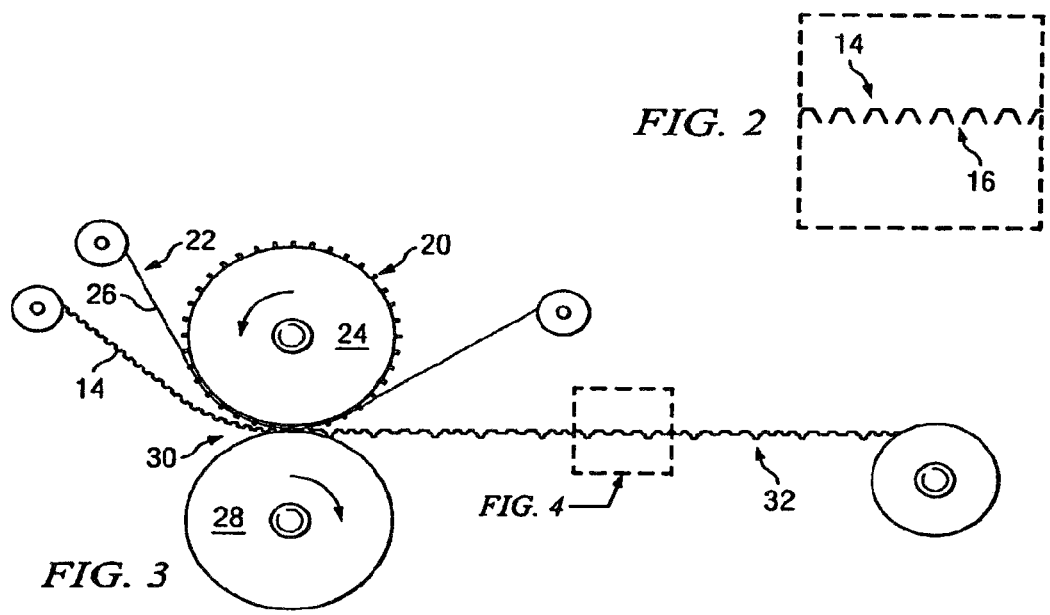
FIG. 3
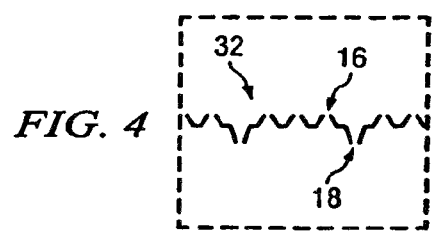
FIG. 4

APERTURED MATERIAL FOR USE IN ABSORBENT ARTICLES

CROSS-REFERENCE TO RELATED APPLICATIONS

This application claims priority to application U.S. Ser. No. 10/744,152, filed Dec. 22, 2003, which claims priority to provisional application U.S. 60/435,942, filed Dec. 20, 2002. The aforementioned applications are incorporated herein by reference.

TECHNICAL FIELD

This invention relates to the formation of three-dimensional thermoplastic films, and more particularly those with both micro-texture and macro-apertures.

BACKGROUND

Description of Related Art

There has always been a need to create cloth-like textures in poly-olefin films that can in turn become three-dimensionally apertured fluid transporting structures. In the past this texturing was achieved through the creation of a plurality of micro-apertures that stick out from the surface of film. This fragile micro-texture can be created through the use of water forming or vacuum forming as described in the prior art. However, once micro-texturing is completed, it is difficult to create the three-dimensional ("3D") funnel-shaped aperture that allows the fluid to pass through the film into the absorbent layer underneath without destroying the micro-texture. Water or needle perforation has been attempted, however, the water approach is not at a high enough temperature to create a permanently deformed and stress annealed aperture. Thus, a large 3D aperture formed using water perforation could have the tendency to become flat again if subjected to stress or to pressure at the time the aperture is formed. Use of a hot needle is not effective either, because the heat from the hot needle will melt the surrounding, very delicate micro-texture if the needle is hot enough to impart any permanent deformation into the cone. If the micro-texture is micro-apertures, the heat of the needle causes the edges of the micro-apertures to "crisp" or become very stiff as a result of the exposure to the heat. This sort of stiffening of the edges makes the final product rough to the touch.

A novel method of using thermo-mechanical perforation with a matching set of needles, grooves and protective surface to create such product is disclosed herein. Further, this invention teaches how, in one pass, a product can have large 3D fluid transport holes imparted into a micro-textured film and how a fluid transport layer may be attached under the fluid transport sheets to direct the fluid away from the 3D funnel of the micro-textured film. The final product produced via such process is primarily intended for use as a body-contacting, textured formed film top sheet in an absorbent hygienic product or wound dressing. Further, this product can be used as a sub-layer in such an absorbent article or as a top layer in a baby diaper.

SUMMARY

A film is first microscopically textured and then macroscopically textured while maintaining the microscopic texture. The micro-texturing may be done by a variety of means including vacuum forming, and may include micro-apertures. The macroscopic texture may be done by a variety of means including thermo-mechanical means with a heat shielding means. Where heated pins are used, the heat shielding means protects the micro-texture from the heat so that the heat does not deform the micro-texture.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic view of a method of forming a micro-texture in a film.

FIG. 2 is a cross sectional view of a film with micro-texture formed by the process shown in FIG. 1.

FIG. 3 is a schematic view of a method of forming a macro-texture in a film.

FIG. 4 is a cross sectional view of a film with both a micro-texture and a macro-texture as formed by the processes of FIG. 1 and FIG. 3.

Like reference symbols in the various drawings indicate like elements.

DETAILED DESCRIPTION

Figure 5:
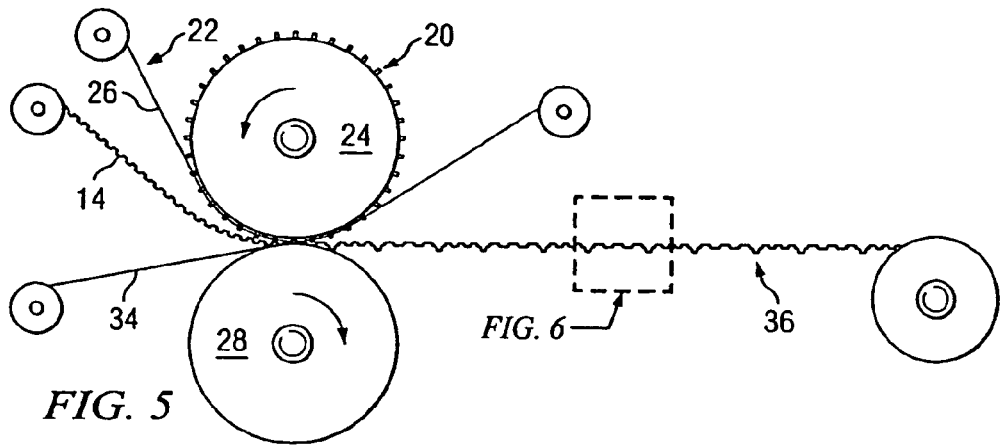
FIG. 5 is a schematic view of a method of forming a macro-texture in a film while combining a nonwoven layer with the film.

As used herein, "micro" refers to individual features that are not individually discernable, when viewed by the human eye from about 18 inches, although a change in texture on a whole may be discernable, while "macro" refers to features that are individually discernable when viewed by the human eye from about 18 inches. For example, micro-apertures with a mesh of between about 30 apertures per linear inch and 100 apertures per linear inch will change the surface texture of a film, but the individual apertures will not be individually discernable by the human eye from a distance of about 18 inches. Likewise, macro-apertures with a spacing of about 5 to about 11 holes per square centimeter will be individually discernable by the human eye from a distance of about 18 inches.

A film material 10, which is typically thermoplastic, is extruded onto a forming screen 12. Forming screen 12 contains a micro-texture. The forming screen 12 may have a variety of micro-texture patterns. The film material 10 is thereby formed into a microscopically three-dimensional film 14. The film material 10 may be apertured as part of the vacuum forming or may be allowed to stay intact.

The film material 10 may be a thin film consisting of a 50/50 blend of LDPE and LLDPE extruded from a cast die 116 or a blown die. While the film material 10 is still in a semi-molten, malleable state a pressure is applied by differential pressure means, such as a vacuum, blown air, etc., to the film material 10 to have the film material 10 form to a screen 12. The pressure may be applied by known vacuum forming techniques as shown in FIG. 1, although other means may be acceptable. The screen 12 imparts a micro-texture 16 to the film material 10. The resultant micro-textured film 14 will have a micro-texture 16, which may include micro-apertures, micro-ridges, micro-dots, or other micro-textures known in the art, as it is removed from the screen 12 as shown in FIG. 2. If the micro-texture 16 is micro-apertures, the micro-apertures may have a density of between about 30 holes per linear inch and about 100 holes per linear inch, also known as about 30 mesh to about 100 mesh, and preferably between about 40 mesh and about 60 mesh. Where micro-textures 16 are formed of micro-apertures, they may be three-dimensional micro-funnels to increase their effect on tactile response as well as fluid handling properties. Where micro-textures 16 are formed of micro-apertures they may be round; elongated, octagonal, oval, hexagonal, ellipsoid, rectangular, square, or any other shape or pattern depending on the preferred texture or fluid handling properties.

The film material 10 may contain surfactants in the resin, or surfactants may be added to the micro-textured film 14. Surfactants increase the philicity of the normally phobic film material 10 and may affect the performance of the finished product as discussed below. Alternatively, surfactants may not be added, resulting in a phobic film material 10.

In a preferred embodiment, the micro-textured film 14 is then thermo-mechanically perforated to produce a macroscopic three-dimensional aperture 18. The macro-aperture 18 forms a macroscopic texture on the film, and therefore the terms macro-texture and macro-aperture 18 are used throughout. Heat shielding 22 allows the use of heated pins 20 to perforate the micro-textured film 14 without destroying the micro-texture 16. Without heat shielding 22, the heated pins 20 may soften the material of film 14 such that micro-texture 16 is destroyed or the heated pins 20 may crisp the edges of the micro-texture 16 as described above. If micro-textured film 14 is sufficiently heated by heated pins 20, the micro-texture 16 will melt back to a film, thus losing the texture created by screen 12. The heat shield 22, shown in FIGS. 3, 5, 7, and 9, is a shielding material 26 having a higher melting point than the film, such as a nonwoven polypropylene, which passes through the perforating nip 30 between the micro-textured film 14 and a drum 24 carrying heated perforating pins 22. Two effective examples of shielding material 26 are nonwovens known in the art as Spun-Meltblown-Spun 19 gsm and Thermo-bonded Carded 24 gsm. The selection of an appropriate nonwoven material to be used as shielding material 26 should be based on finding a nonwoven that has a melting point higher than the film material 10. Other heat shields would include various other materials, which may be able to run on a continuous loop with a cooling cycle, a cooled drum/heated pin arrangement, and various fluid-cooling means.

The thermo-mechanical perforating unit shown in FIG. 3 uses heated pins 20 mated into an unheated female roll 28 to form a nip 30. The micro-textured film 14 and above-mentioned shielding material 26 are fed into the nip 30 such that the heated pins 20 form macroscopic three-dimensional apertures 18 in the micro-textured film 14. The shape of the apertures is determined by the relationship between pins 20 and roll 28. The macro-apertures 18 of this preferred embodiment have a density of between about 4 holes per square centimeter and about 15 holes per square centimeter, and preferably between about 5 holes per square centimeter and about 12 holes per square centimeter. The macro-apertures 18 may be formed into a cone that extends from an upper surface of the film 14 to a lower surface spaced apart by a distance greater than the initial thickness of film 14. The taper of the cone will depend on the shape of female roll 28 and heated pins 20. Depending on the relative speed at which the film 14, heated pins 20, and female roll 28 are moving, the macro-apertures 18 may be round or elongated.

Female roll 28 may be temperature controlled to maintain a consistency to the macro-apertures 18 formed at the nip 30. The temperature control may include cooling or heating as needed for the desired results. For example, an operating temperature of 30 degrees Celsius may require cooling in some environments, heating in others.

Figure 6:
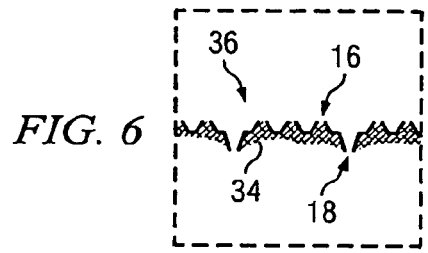
FIG. 6 is a cross sectional view of a film adjacent to a nonwoven layer and with both a microtexture and a macro-texture as formed by the processes of FIG. 1 and FIG. 5.
Figure 7:
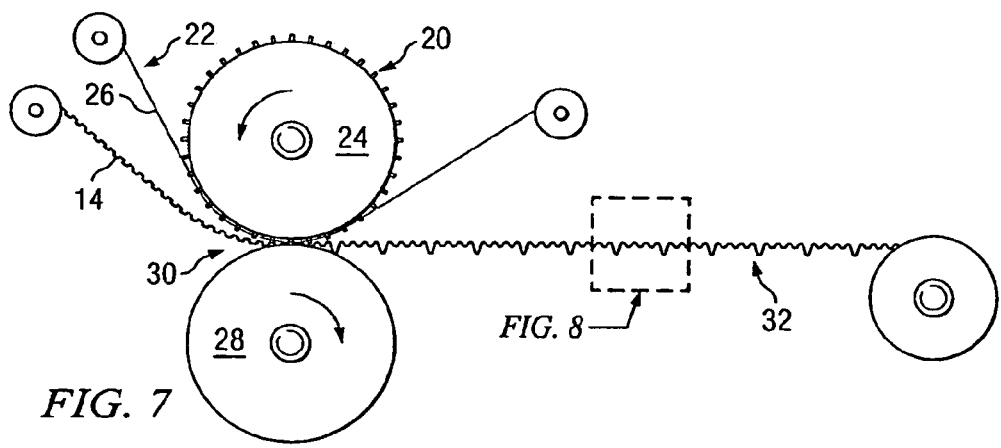
FIG. 7 is a schematic view of a method of forming a macro-texture in a film.
Figure 8:
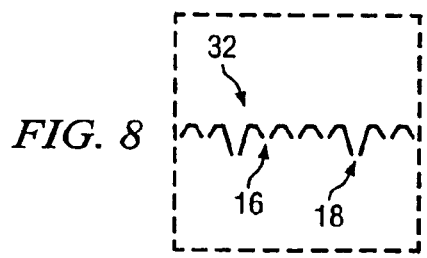
FIG. 8 is a cross sectional view of a film with both a micro-texture and a macro-texture as formed by the processes of FIG. 1 and FIG. 7.

The film 32 of the preferred embodiment will have a vacuum formed micro-texture 16 and a thermo-mechanically formed macro-texture 18, as shown in FIGS. 4 and 8. The micro-textured film 14 of FIG. 2 has a caliper of about 25 microns while the caliper of the film 32 of FIGS. 4 and 6 is about 400 microns to about 1500 microns, preferably between about 800 microns and 1300 microns. The film 32 of this preferred embodiment will have a desirable texture provided by the micro-texture 16 and a resilient structure provided by the macro-texture 18.

Figure 9:
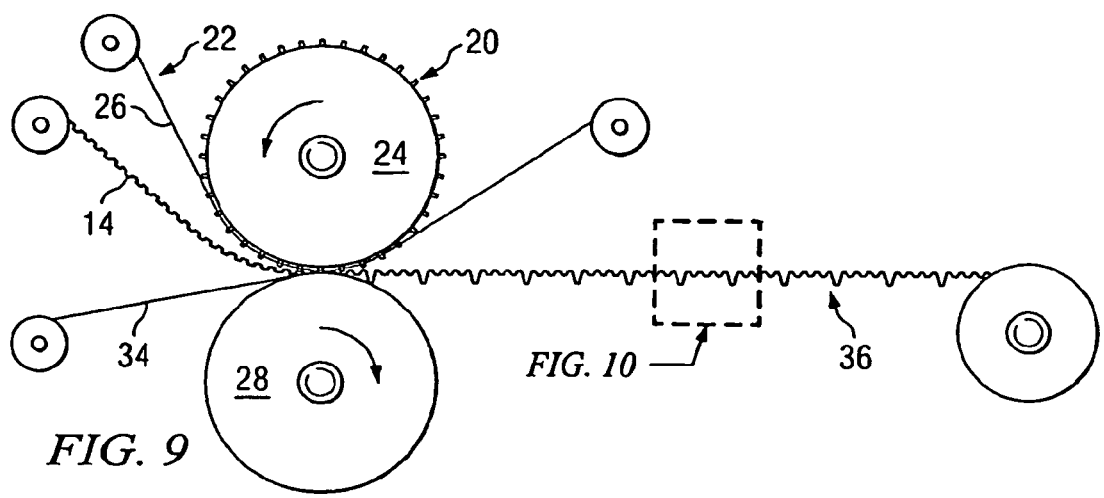
FIG. 9 is a schematic view of a method of forming a macro-texture in a film while combining a nonwoven layer with the film.

As shown in FIGS. 5 and 9, a second material 34, such as a wicking nonwoven, may be fed into the nip 30 of the thermo-mechanical forming means to simultaneously bond the second material 34 to the film layer 14 thus creating a composite material 36. The second material 34 may be positioned between the film layer 14 and female roll 28 so that the micro-texture 16 is still exposed. Heated pins 20 would puncture second material 34 at macro-apertures 18. In this manner, a composite, material 36 may be formed having the tactile impression and fluid handling abilities of a micro-apertured film backed by a wicking material and the fluid handling abilities of macro-apertures 18 unobstructed by the second material 34 as shown in FIG. 6. The second material 34 is effective in wicking moisture away from the film layer 14, thus improving the wetback performance.

Figure 10:
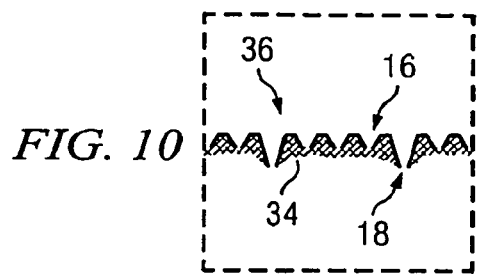
FIG. 10 is a cross sectional view of a film adjacent to a nonwoven layer and with both a microtexture and a macro-texture as formed by the processes of FIG. 1 and FIG. 9.

As can be seen by comparison of FIGS. 4 and 8 or FIGS. 6 and 10 where the micro-textures 16 are micro-apertures, the micro-apertures may extend in the same direction as the macro-apertures 18, FIGS. 8 and 10, or in the opposite direction as the macro-apertures 18, FIGS. 4 and 6.

Absorbent articles typically have a body facing topsheet, a backsheet opposite the topsheet, and an absorbent core between the topsheet and backsheet. Additionally, modern absorbent articles may contain an intermediate layer between the topsheet and the absorbent core. The film 32 or composite material 36 may be used as a topsheet or an intermediate layer in an absorbent article.

Performance Measures

Various materials were tested as topsheets against comparative topsheet materials. One of the comparative materials is a hydro-formed topsheet used in the Procter & Gamble sanitary napkin product "Lines Petalo Blu" and referred to herein as "HFF". Another of the comparative materials is the nonwoven phobic topsheet used in the SCA sanitary napkin product "Nuvenia Libresse" and referred to herein as "NW". The materials used for the different examples are as follows:

Example 1: A micro-texture 16 of 60 mesh micro-apertures in a philic film material 10 and macro-apertures 18 with a spacing of about 5.6 apertures per square centimeter.

Example 2: Similar to Example 1, but with a micro-texture 16 of 40 mesh micro-apertures.

Example 3: Similar to Example 1, but with a phobic film material 10.

Example 4: Similar to Example 2, but with a phobic film material 10.

Example 5: Similar to Example 1, but with a second material 34 of 25 gsm air through bonded nonwoven (ATB 25 RAM).

Example 6: Similar to Example 2, but with a second material 34 of 25 gsm air through bonded nonwoven (ATB 25 RAM).

Example 7: Similar to Example 5, but with macro-apertures 18 with a spacing of about 11 apertures per square centimeter.

Example 8: Similar to Example 6, but with macro-apertures 18 with a spacing of about 11 apertures per square centimeter.

Strikethrough is a measure of the rate of absorption through a topsheet into an absorbent article and was conducted on finished articles as indicated below. In order to test strikethrough the original topsheet material is removed from the article and replaced with the topsheet material to be tested, except when testing the sample of the original material. The article is then insulted with a 10 ml sample of Menstrual Internal Synthetic Solution (MISS) and the strikethrough time is recorded using a Lister apparatus as described in EDANA Recommended Test Method ERT 150.5-02 Liquid Strike Through Time Test Method. Lower strikethrough numbers reflect a fast absorption and are desired in most absorbent articles.

Wetback is measured on the same samples used in the strikethrough test described above. After the strikethrough is measured the samples are carefully removed from the test apparatus and positioned on a flat surface. A 4 kg weight with a surface of 10 cm by 10 cm is placed on the insult area of the sample for three minutes. At three minutes the weight is removed and 5 pre-weighed pick up papers are placed over the insult area and the weight is placed over the pickup paper. At two minutes the weight is removed and the pickup paper is removed and reweighed The weight gained by the pickup paper is reported as the wetback. This method is based on EDANA Recommended Test Method ERT 151.3-02 Wetback. Lower wetback numbers reflect more complete absorption and less leakage to the insult surface and are desired in most absorbent articles.

The following data refers to the tests performed on "Lines Petalo Blu" articles tested under the method described above:

| Topsheet | Strikethrough (seconds) | Rewet (grams) |
| --- | --- | --- |
| HFF | 49.0 | 0.93 |
| Example 1 | 38.7 | 0.72 |
| Example 2 | 13.0 | 0.36 |
| Example 5 | 54.8 | 0.43 |
| Example 6 | 27.8 | 0.27 |
| Example 7 | 47.0 | 0.42 |
| Example 8 | 32.0 | 0.26 |

The following data refers to the tests performed on "Nuvenia" articles tested under the method described above:

| Topsheet | Strikethrough (seconds) | Rewet (grams) |
| --- | --- | --- |
| NW | >500 | 1.3 |
| Example 1 | 143.6 | 1.2 |

-continued

| Topsheet | Strikethrough (seconds) | Rewet (grams) |
| --- | --- | --- |
| Example 2 | 73.4 | 1.2 |
| Example 3 | 325.3 | 1.1 |
| Example 4 | 164.0 | 1.1 |
| Example 7 | 91.78 | 0.465 |
| Example 8 | 61.13 | 0.570 |

As can be seen from the above results, all of the Examples showed improvement over the original topsheet material used in the absorbent article.

While particular embodiments of the present invention have been illustrated and described, it would be obvious to those skilled in the art that various other changes and modifications can be made without departing from the spirit and scope of the invention. The appended claims are therefore intended to cover all such changes and modifications that are within the scope of this invention.

What is claimed is:

1. A method comprising:
supplying a thin film of molten polymer to a forming screen;
applying a pressure differential to said thin film to form a micro-texture on a surface of the film; said microtexture comprising a plurality of protrusions originating on the surface of the film and extending outwardly therefrom;
applying a nonwoven fibrous web against the micro-textured surface of said film;
feeding said nonwoven fibrous web and said film into a nip formed between a heated pin roller and a female counter roller, said female counter roller having openings therein to receive the pins from said pin roller;
urging pins on said heated pin roller through said nonwoven web and said micro-textured film to form macro apertures in said film, said macro apertured comprising conical shaped members protruding away from said film;
separating the nonwoven web from the micro-texture surface on said film; wherein the micro-textured surface of said film is not damaged during said macro-aperture formation step.

2. The method of claim 1, wherein said heat shield nonwoven fibrous web is unwound from a roll, fed through the nip, removed from contact with the heated pin roller, and wound on a separate roll.

3. The method of claim 1 wherein said macro apertures have a spacing of about 4 to about 15 apertures per square centimeter.

4. The method of claim 1 wherein said micro-textured surface and macro apertured film has a caliper of about 400 microns to about 1500 microns.

5. The method of claim 1 wherein said micro-texture is selected from the group consisting of microscopic three-dimensional apertures, micro-ridges, and micro-dots.

6. The method of claim 5 wherein said microscopic three-dimensional apertures are micro-funnels.

7. The method of claim 6 wherein said microscopic three-dimensional apertures have a spacing of about 30 to about 100 apertures per linear inch.

8. The method of claim 1 further comprising the step of continuously removing the nonwoven web from the heated pin roller after macro aperturing said film.

9. The method of claim 1 wherein said nonwoven fibrous web is polypropylene.

10. The method of claim 1 wherein said counter roller is a cooled drum.

11. The method of claim 1 wherein said macro apertures protrude away from the film in a direction opposite the micro-texture of said film.

12. The method of claim 1, further comprising the step of supplying a web of a second material prior to feeding said film into said nip, wherein said second material is located adjacent a surface of the film without micro-texture.

13. The method of claim 12 wherein said second material is a nonwoven web of fibers.

14. The method of claim 13 wherein said second material is bonded to and co-apertured with said film simultaneously with said macro aperture formation to form a composite material.

* * * * *